United States Patent
Ford

(10) Patent No.: US 11,918,190 B2
(45) Date of Patent: Mar. 5, 2024

(54) SPECULUM SLEEVE

(71) Applicant: NEW YORK UNIVERSITY, New York, NY (US)

(72) Inventor: Jacqueline F. Ford, Roslyn Heights, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 17/835,493

(22) Filed: Jun. 8, 2022

(65) Prior Publication Data

US 2022/0296091 A1    Sep. 22, 2022

Related U.S. Application Data

(62) Division of application No. 16/134,015, filed on Sep. 18, 2018, now Pat. No. 11,369,260.

(60) Provisional application No. 62/559,730, filed on Sep. 18, 2017.

(51) Int. Cl.
| | |
|---|---|
| *A61B 1/32* | (2006.01) |
| *A61B 1/00* | (2006.01) |
| *A61B 1/303* | (2006.01) |
| *A61M 29/02* | (2006.01) |

(52) U.S. Cl.
CPC .......... *A61B 1/32* (2013.01); *A61B 1/00082* (2013.01); *A61B 1/00135* (2013.01); *A61B 1/303* (2013.01); *A61M 29/02* (2013.01)

(58) Field of Classification Search
CPC .................................. A61B 1/303; A61B 1/32
See application file for complete search history.

(56) References Cited

U.S. PATENT DOCUMENTS

| | | | |
|---|---|---|---|
| 5,090,958 A | 2/1992 | Sahota | |
| 5,545,122 A | 8/1996 | Spruill | |
| 5,601,590 A | 2/1997 | Bonutti | |
| 5,716,329 A * | 2/1998 | Dieter | .............. A61B 1/303 |
| | | | 600/184 |
| 6,364,832 B1 | 4/2002 | Propp | |
| 6,432,048 B1 | 8/2002 | Francois | |
| 7,063,664 B2 | 6/2006 | Mohajer | |
| 8,652,035 B2 | 2/2014 | Steigerwald | |

(Continued)

OTHER PUBLICATIONS

ClinicalTrials.gov Using a Sheathed Speculum to Visualize and Access the Cervix in Women With Excessive Vaginal Tissue, NCT00595166, Apr. 6, 2016, 6 pages.

(Continued)

*Primary Examiner* — Julianna N Harvey
(74) *Attorney, Agent, or Firm* — Riverside Law LLP

(57) ABSTRACT

The present invention relates to expandable sleeves, expandable sleeve systems, and their methods of use. In certain aspects, the expandable sleeves are compatible with commonly used speculums to enhance visualization and access of an orifice. The expandable sleeves sheathe over the blades of a speculum and form a taut barrier when the blades are opened to hold back the walls of a tissue orifice and cavity. The expandable sleeves include inflatable pouches that further push back the walls of the orifice. In certain aspects, the expandable sleeves are useful in performing pelvic exams, such as in patients having lax vaginal walls or excess surrounding tissue.

7 Claims, 3 Drawing Sheets

(56) References Cited

U.S. PATENT DOCUMENTS

| | | | |
|---|---|---|---|
| 8,721,534 B1* | 5/2014 | Luecke | A61B 1/00148 |
| | | | 600/184 |
| 2002/0013601 A1 | 1/2002 | Nobles | |
| 2005/0124860 A1* | 6/2005 | Mohajer | A61B 1/303 |
| | | | 600/203 |
| 2008/0081951 A1 | 4/2008 | Frasier | |
| 2012/0130179 A1 | 5/2012 | Rockrohr | |
| 2019/0000310 A1* | 1/2019 | Prendiville | A61B 1/32 |

OTHER PUBLICATIONS

Four-Way Vaginal Exapanders, Utah Medical Products Inc. http://www.utahmed.com/pdf/58213.pdf, Accessed: Sep. 13, 2019, 2 pages.
Hill et al. "Sheathed versus standard speculum for visualization of the cervix." Int J Gynaecol Obstet May 2014;125(2):116-20. doi: 10.1016/j.ijgo.2013.10.025. Epub Feb. 1, 2014.
PELIspec Pro-Wall, Pelican Feminine Healthcare, http://www.pelicanfh.co.uk/product/pelispec-pro-wall, Accessed Sep. 13, 2019, 8 pages.

* cited by examiner

SPECULUM SLEEVE

CROSS REFERENCE TO RELATED APPLICATIONS

This application is a divisional of U.S. patent application Ser. No. 16/134,015, filed Sep. 18, 2018, which claims priority to U.S. Provisional Patent Application No. 62/559,730, filed Sep. 18, 2017, each of which are hereby incorporated by reference herein in their entirety.

BACKGROUND OF THE INVENTION

Adequate visualization of the cervix and vaginal apex is necessary for the performance of many routine obstetric and gynecologic procedures, such as pap spear testing, colposcopy, cervical biopsies, and evaluation of lesions, tumors, and cancerous growths of the cervix, endocervix, and uterine lining. Currently, speculum designs do not adequately address the laxity in the vaginal walls to allow full visualization of the cervix in both obese and morbidly obese obstetrics and gynecology (ob/gyn) patients. Attempts to address this issue include lateral vaginal wall retractors. These are often made of metal and are uncomfortable, cumbersome, space occupying, expensive, and require autoclaving. The lateral vaginal wall retractors provide incomplete exposure, as they are unable to prevent vaginal wall collapse in the gaps between the retractors.

There is a need for a device to improve visualization and access of orifices. The present invention addresses this need.

SUMMARY OF THE INVENTION

In one aspect, the present invention relates to an expandable sleeve, comprising: a tubular member formed of an expandable material having a length, an internal surface, and an external surface; and opposing inflatable pouches formed of an expandable material positioned on the exterior surface of the tubular member.

In one embodiment, the sleeve further comprises at least one partition wall connected to the internal surface of the tubular member to form at least two lumens within the tubular member, wherein the opposing inflatable pouches are positioned adjacent to one of the at least two lumens. In one embodiment, the at least one partition wall includes an upper partition wall and a lower partition wall each connected to the internal surface off the tubular member to form an upper lumen, a central lumen, and a lower lumen within the tubular member, and wherein the opposing inflatable pouches are positioned adjacent to the central lumen.

In one embodiment, the expandable material is a biocompatible material. In one embodiment, the expandable material is an elastomer. In one embodiment, the expandable material is a thermoplastic elastomer. In one embodiment, the expandable material is a United States Pharmacopeia (USP) Class VI Medical Grade Plastic Material. In one embodiment, the expandable material is selected from the group consisting of: silicone, latex, nylon, polyethylene, polyethylene terephthalate (PET), urethane, polyurethane, polypropylene, nitrile, fluoroelastomer, ethylene propylene diene monomer (EPDM), styrenic block copolymer, copolyester, polyamide, polyolefin, and combinations thereof. In one embodiment, the expandable material comprises a coating.

In one embodiment, the inflatable pouches have greater elasticity than the tubular member. In one embodiment, the inflatable pouches have a textured exterior surface. In one embodiment, the inflatable pouches each have a length that is equal to or less than the length of the tubular member. In one embodiment, a plurality of inflatable pouches are positioned lengthwise in parallel along the length of the tubular member. In one embodiment, the length of each of the inflatable pouches is divided by individually inflatable segments.

In one embodiment, the inflation pouches are each fluidly connected to an inflation lumen. In one embodiment, the inflation lumens merge into a single lumen that terminates in a luer lock connectable to an inflation pump. In one embodiment, the luer lock comprises a stopcock or a check valve. In one embodiment, the inflation pump is a syringe or a reciprocating pump. In one embodiment, the inflation pump pumps a gas or a liquid.

In another aspect, the present invention relates to an orifice access system, comprising: a sleeve comprising a tubular member formed of an expandable material having a length, an internal surface, an external surface, and opposing inflatable pouches positioned on the exterior surface of the tubular member; a speculum having a handle and blades, the blades being sized to fit within the sleeve; and an inflation pump.

In one embodiment, the inflation pump is incorporated into the speculum handle. In one embodiment, the system further comprises an inflation media selected from a gas or a liquid. In one embodiment, the system further comprises a lubricant.

In another aspect, the present invention relates to a method of accessing an orifice, comprising the steps of: providing a sleeve comprising a tubular member formed of an expandable material having a length, an internal surface, an external surface, and opposing inflatable pouches positioned on the exterior surface of the tubular member; providing a speculum having blades sized to fit within the sleeve; fitting the blades into the sleeve such that the inflatable pouches are folded between the blades; inserting the blades and the sleeve into an orifice; expanding the blades and the sleeve within the orifice; and inflating the inflatable pouches.

In one embodiment, the blade and sleeve are inserted into a vagina, thereby providing access to the cervix, endocervix, and endometrium. In one embodiment, the inflatable pouches are at least partially deflated to enable repositioning of the sleeve within the orifice.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
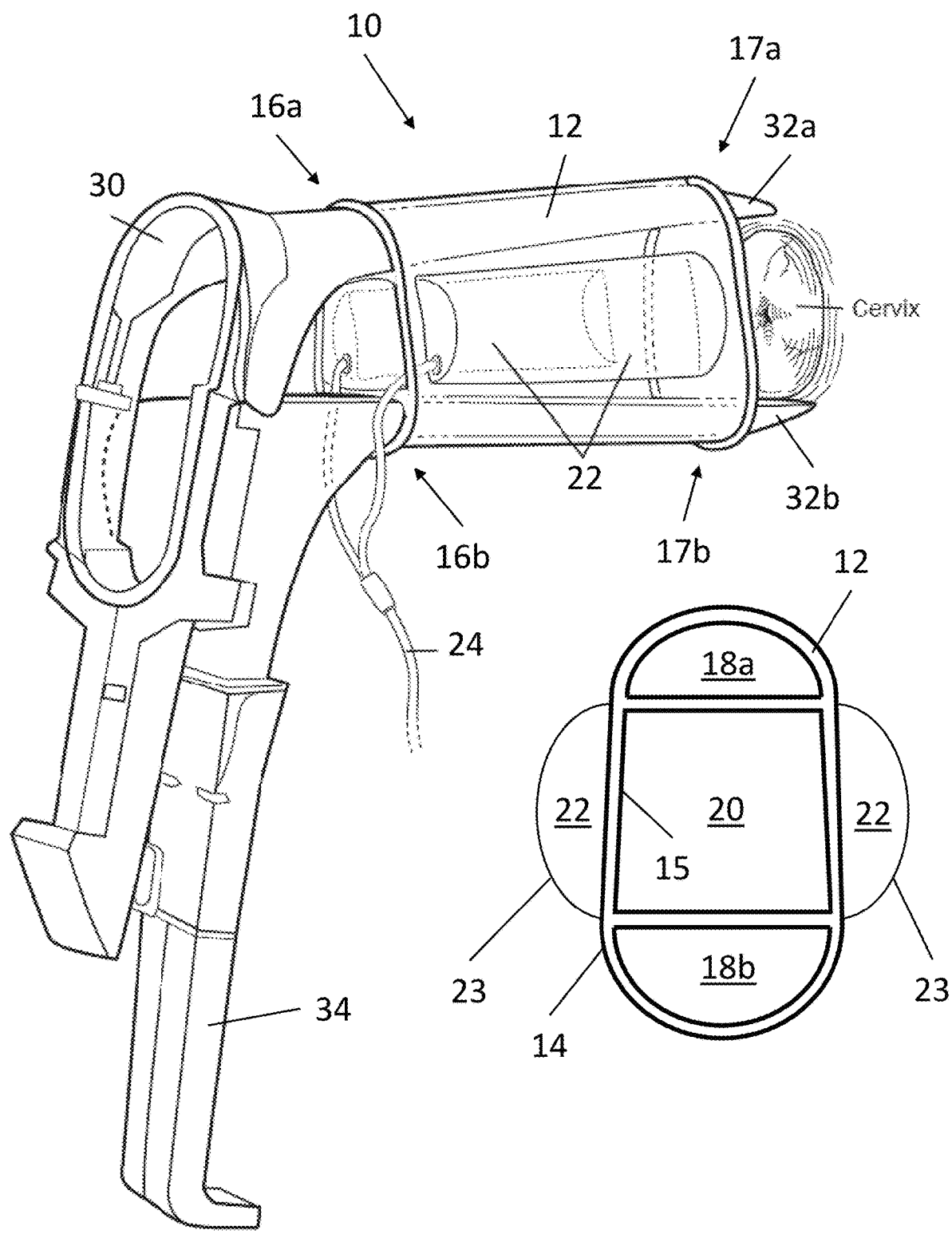
FIG. 1 depicts an exemplary expandable sleeve deployed on a speculum, and a cross-section view of the deployed expandable sleeve.

The present invention relates to expandable sleeves, expandable sleeve systems, and their methods of use. In certain aspects, the expandable sleeves are compatible with commonly used speculums to enhance visualization and access of an orifice. In some embodiments, the expandable sleeves sheathe over the blades of a speculum and form a taut barrier when the blades are opened to hold back the walls of a tissue orifice and cavity. The expandable sleeves include inflatable pouches that further push back the walls of the orifice. In certain aspects, the expandable sleeves are useful in performing pelvic exams, such as in patients having lax vaginal walls or excess surrounding tissue.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Expandable Sleeve

The present invention includes expandable sleeves. Referring now to FIG. 1, an exemplary expandable sleeve 10 is depicted. Expandable sleeve 10 comprises a tubular member 12 having a length, an exterior surface 14, and an interior surface 15. The interior of the tubular member 12 comprises a lumen 20 connected to an open distal upper end 16a and lower end 16b and to an open proximal upper end 17a and lower end 17b. In some embodiments, tubular member 12 comprises at least one partition wall connected to interior surface 15, providing one or more additional lumens 18 to the interior of tubular member 12. For example, in the embodiment depicted in FIG. 1, the interior of tubular member 12 comprises two partition walls, providing lumen 18a (extending from distal upper end 16a to proximal upper end 17a) and lumen 18b (extending from distal lower end 16b to proximal lower end 17b) above and below lumen 20. In some embodiments, lumen 18a and lumen 18b terminate in a closed tip at proximal upper end 17a and lower end 17b, respectively. Tubular member 12 can have any suitable length, such as a length between 50 mm and 120 mm. In various embodiments, tubular member 12 can be sized to fit commonly used speculum types, including the Cusco speculum (typically 65 mm to 105 mm in length), the Grave speculum (typically about 75 mm to 165 mm in length), the Pederson speculum (typically about 75 mm to 170 mm in length), the Weisman speculum (typically about 100 mm in length), the Collins speculum (typically about 95 mm to 115 mm in length), and the Devilbiss speculum (typically about 100 mm in length).

Expandable sleeve 10 further comprises at least one inflatable pouch 22, each inflatable pouch 22 formed by a pouch surface 23 attached to the exterior surface 14 of tubular member 12. In some embodiments, expandable sleeve 10 comprises at least one inflatable pouch 22 positioned opposite from at least one other inflatable pouch 22. For example, in the embodiment depicted in FIG. 1, expandable sleeve 10 comprises two opposing inflatable pouches 22, each inflatable pouch 22 extending for at least a portion of the length of tubular member 12. In some embodiments, expandable sleeve 10 comprises several inflatable pouches 22 on opposing sides of tubular member 12, each inflatable pouch 22 extending for at least a portion of the length of tubular member 12 and arranged in parallel to each other (not pictured). In some embodiments, each inflatable pouch 22 is divided along its length into individually inflatable segments (not pictured). In some embodiments, expandable sleeve 10 can include a combination of one or more inflatable pouches 22 on opposing sides of tubular member 12, the one or more inflatable pouches 22 extending for at least a portion of the length of tubular member 12, being divided along its length into individually inflatable segments, or both.

Each inflatable pouch 22 or inflatable segment is fluidly connected to an inflation lumen 24 terminating in a connector. In some embodiments, two or more inflation lumens 24 merge into a single connector, such that multiple inflatable pouches 22 or inflatable segments may be inflated and deflated simultaneously. The connector can be any suitable connector, such as a luer lock. The connector can further include a flow arresting mechanism, such as a stopcock or a check valve. The connector is joinable to an inflation pump and a source of inflation media. The inflation pump can be any suitable pump capable of reversibly transporting an inflation media, such as a syringe or a reciprocating pump. The inflation media can be a gas (such as air) or a liquid (such as water or saline). The inflation media can be stored in a reservoir. In certain embodiments, the reservoir can include a temperature regulator, such as a heating or a cooling element.

Tubular member 12 and pouch surface 23 are constructed from any suitable expandable material. In some embodiments, the expandable material is an elastomer. In some embodiments, the expandable material is a thermoplastic elastomer. In some embodiments, the expandable material is a biocompatible material, such as a United States Pharmacopeia (USP) Class VI Medical Grade Plastic Material. Non-limiting examples of the expandable material include: silicone, latex, nylon, polyethylene, polyethylene terephthalate (PET), urethane, polyurethane, polypropylene, nitrile, fluoroelastomer, ethylene propylene diene monomer (EPDM), styrenic block copolymer, copolyester, polyamide, polyolefin, and combinations thereof. In some embodiments, the expandable material is at least partially transparent.

Figure 2:
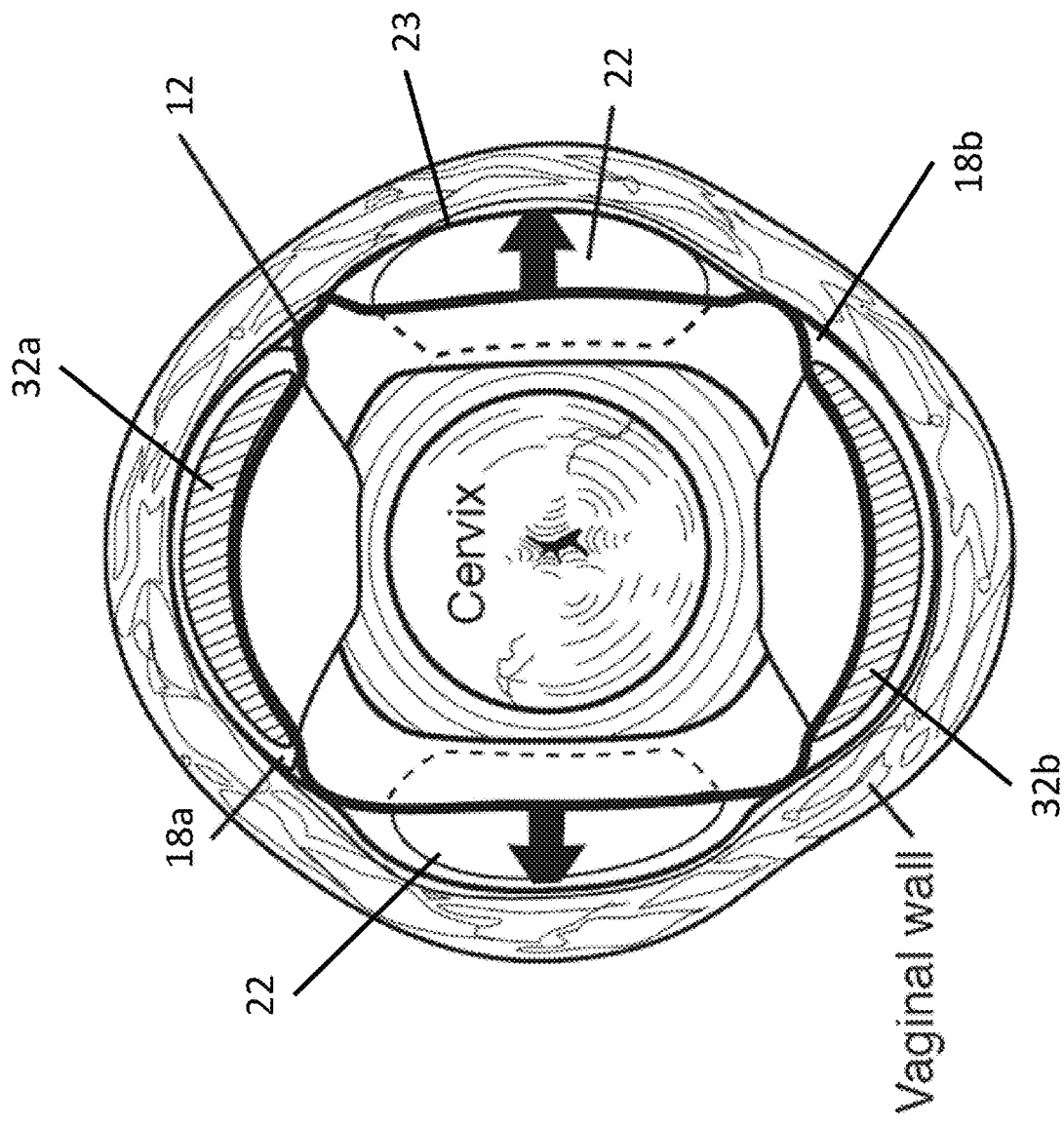
FIG. 2 depicts a cross-sectional perspective view of an exemplary expandable sleeve deployed within a vagina.

In certain embodiments, pouch surface 23 has a greater elasticity than tubular member 12. A greater elasticity enables pouch surface 23 to distend in a direction away from tubular member 12 when inflatable pouches 22 are inflated, and enables tubular member 12 to support the inflated pouches 22 without obstructing lumen 20 (FIG. 2). The difference in elasticity can be achieved through several means, such as by making pouch surface 23 and tubular member 12 from expandable materials having different levels of elasticity, or by making tubular member 12 from a thicker layer of an expandable material.

Expandable sleeve 10 is amenable to any modification to augment its function. For example, in some embodiments, exterior surface 14, pouch surface 23, or both can include texturing or ridges to enhance grip on the walls of an orifice. In some embodiments, interior surface 15 can include texturing or ridges to enhance the fit of expandable sleeve 10 on a speculum. In some embodiments, the several surfaces of expandable sleeve 10 can include a coating. Non-limiting coatings include therapeutic coatings (e.g., anesthetic, antimicrobial, antibacterial, antifungal, or antiviral), hygienic coatings (e.g., sterile or scented), and comfort-improving coatings (e.g., lubricated, heated, or cooled). In various embodiments, tubular member 12 and pouches 22 can be constructed from different materials, or have regions of exterior surface 14, interior surface 15, and pouch surface 23 constructed from different materials. For example, in some embodiments the region of exterior surface 14 covered by pouches 22 can constructed from a material different than the rest of exterior surface 14.

Expandable Sleeve and Speculum System

The present invention also includes systems comprising expandable sleeves and speculums. The system combines features of the expandable sleeve with a speculum to provide a single streamlined instrument for enhanced visualization of orifices.

In some embodiments, the system comprises an expandable sleeve 10 and a typical speculum, such as speculum 30 depicted in FIG. 1. Speculum 30 comprises top blade 32a and bottom blade 32b connected by a hinge and actuated by handle 34. Blades 32a and 32b are sized to fit within lumen 20 of expandable sleeve 10 and are constructed from a rigid material, such as a plastic or a metal, capable of supporting a stretched expandable sleeve when opened. In some embodiments, blades 32a and 32b are sized to fit within one or more partition lumen 18. For example, in FIG. 1, the depicted top blade 32a is sized to fit within lumen 18a and bottom blade 32b is sized to fit within lumen 18b. The lumens 18a and 18b aid in orienting inflatable pouches 22 such that the inflatable pouches 22 are positioned lateral to blades 32a and 32b.

In certain embodiments, the system integrates features of expandable sleeve 10 into speculum 30. For example, in some embodiments, the portion of expandable sleeve 10 that contains inflatable pouches 22 can be built into blades 32a and 32b in a manner similar to the cheeks of a mouth. In these embodiments, at least one piece of expandable material connects the left lateral edges of top blade 32a to bottom blade 32b, and at least one piece of expandable material connects the right lateral edges of top blade 32a to bottom blade 32b.

In some embodiments, speculum 30 can further include an inflation pump and an inflation media source, wherein the inflation pump reversibly transports the inflation media to and from each inflation pouch 22 by way of inflation lumens 24. In some embodiments, the inflation pump can be integrated into handle 34. In some embodiments, the inflation media source, such as a reservoir, can also be integrated into handle 34. The inflation media reservoir can be loadable or pre-loaded with an inflation media. In some embodiments, the inflation lumens 24 can be integrated into and extend through handle 34, blades 32a and 32b, or both.

In various embodiments, the system further includes one or more features such as a light source, a temperature sensor, a blood pressure sensor, an irrigation system, a suction system, and an image capture system.

Method of Use

The present invention also includes methods of using the expandable sleeves described herein for visualization and access of an orifice. The methods are particularly advantageous in accessing orifices with collapsing walls or material occluding the orifice. In some embodiments, the orifice can be a natural orifice on a body, such as a mouth, an ear canal, a nostril, a vagina, or an anus. In other embodiments, the orifice can be a surgically made orifice or a wound.

Figure 3:
FIG. 3 is a flowchart depicting an exemplary method of accessing an orifice using an expandable sleeve and a speculum.

Referring now to FIG. 3, an exemplary method 100 of accessing an orifice using an expandable sleeve and a speculum is depicted. Method 100 beings with step 110, wherein a sleeve comprising a tubular member and opposing inflatable pouches is provided. As described elsewhere herein, the tubular member is formed of an expandable material having a length, an internal surface, and an external surface, and the opposing inflatable pouches are positioned on the exterior surface of the tubular member. In step 112, a speculum having blades sized to fit within the expandable sleeve is provided. In step 114, the blades of the speculum are fitted into the sleeve such that the inflatable pouches are folded between the blades. In this manner, the expandable sleeve is wrapped closely around the blades to minimize its cross-sectional size and to facilitate insertion. In step 116, the blades and the sleeve are inserted into an orifice. In step 118, the blades and the sleeve are expanded within the orifice. In this step, the expansion of the blades holds the expandable sleeve taut, and the taut portion of the sleeves bridging the gap between the blades prevents the orifice from collapsing into the space between the blades. In step 120, the inflatable pouches are inflated, thereby pushing the orifice walls away from the taut portion of the sleeves, increasing the viewable space of the orifice. Optionally, the inflatable pouches can be partially deflated to facilitate repositioning of the sleeve and speculum.

In some embodiments, method 100 can be applied in a pelvic exam, wherein the steps are useful for visualization and access to a subject's cervix, endocervix, and endometrium. For example, step 116 can be adapted to insert the blades of a speculum fitted into the sleeve of the present invention into a subject's vagina, step 118 can be adapted to expand the blades and sleeve within the subject's vagina, and step 120 can be adapted to inflate the inflatable pouches of the sleeve. In some embodiments, the method can further include a step of inserting an instrument into the space created by the expansion of the blades, sleeve, and inflatable pouches, including but not limited to one or more swabs, spatulas, cytobrushes, biopsy curettes, uterine sounds, intrauterine device (IUD) inserters, forceps, and the like.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1: Experimental Expandable Sleeve

The expandable sleeves of the present invention are based in part on an experimental ob/gyn procedure that sheathed a surgical glove over a speculum with the fingertips removed, whereby the surgical glove partially holds back lax lateral vaginal walls when held taut by expanding the speculum blades. A further study compared a procedure using a speculum modified with flexible polypropylene sheath with a standard speculum procedure to assess visualization of the cervix, endocervix, and endometrium and found that the sheathing allowed for full visualization of the cervix in 61.8% of patients versus only 21.6% of patients with a standard speculum. The BMI of the patients in the study was approximately 27±6.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An orifice access system, comprising:
   a sleeve comprising a tubular member having a proximal end and a distal end, the tubular member formed of an expandable material having a length, an internal surface, and an exterior surface; and opposing inflatable pouches formed of an expandable material laterally positioned lengthwise on the exterior surface of the tubular member, such that each inflatable pouch extends from the proximal end to the distal end of the tubular member; wherein the sleeve has a cross-sectional area comprising a cross-section of the tubular member and a cross-section of each of the opposing inflatable pouches, and wherein the opposing inflatable pouches are configured to expand the cross-sectional area of the sleeve in only lateral directions;
   a speculum having a handle and blades, the blades being sized to fit within the sleeve; and
   an inflation pump.

2. The system of claim 1, wherein the inflation pump is incorporated into the speculum handle.

3. The system of claim 1, further comprising an inflation media selected from a gas or a liquid.

4. The system of claim 1, further comprising a lubricant.

5. A method of accessing an orifice, comprising the steps of:
   providing a sleeve comprising a tubular member having a proximal end and a distal end, the tubular member formed of an expandable material having a length, an internal surface, and an exterior surface; and opposing inflatable pouches formed of an expandable material laterally positioned lengthwise on the exterior surface of the tubular member, such that each inflatable pouch extends from the proximal end to the distal end of the tubular member; wherein the sleeve has a cross-sectional area comprising a cross-section of the tubular member and a cross-section of each of the opposing inflatable pouches, and wherein the opposing inflatable pouches are configured to expand the cross-sectional area of the sleeve in only lateral directions;
   providing a speculum having blades sized to fit within the sleeve;
   fitting the blades into the sleeve;
   inserting the blades and the sleeve into an orifice;
   expanding the blades and the sleeve within the orifice; and
   inflating the inflatable pouches.

6. The method of claim 5, wherein the blade and sleeve are inserted into a vagina, thereby providing access to the cervix, endocervix, and endometrium.

7. The method of claim 5, wherein the inflatable pouches are at least partially deflated to enable repositioning of the sleeve within the orifice.

\* \* \* \* \*